United States Patent [19]

Bindel

[11] 4,092,984
[45] June 6, 1978

[54] UNDULATING RECTAL FLUSHING APPARATUS

[76] Inventor: Paul Bindel, 3946 W. North Ave., Chicago, Ill. 60647

[21] Appl. No.: 768,086

[22] Filed: Feb. 14, 1977

[51] Int. Cl.² ............................................. A61M 3/00
[52] U.S. Cl. ................................................ 128/229
[58] Field of Search ............... 128/229, 230, 224, 227, 128/66

[56] References Cited

U.S. PATENT DOCUMENTS

| | | | |
|---|---|---|---|
| 1,983,293 | 12/1934 | Hudgings | 128/227 |
| 2,478,876 | 8/1949 | Nelson | 128/227 |
| 2,506,183 | 5/1950 | Touchberry | 128/227 X |
| 3,042,039 | 7/1962 | Dahlstrom | 128/227 |
| 3,678,932 | 7/1972 | Hudson | 128/227 |
| 3,762,410 | 10/1973 | Bindel | 128/229 |

*Primary Examiner*—John D. Yasko
*Attorney, Agent, or Firm*—Rummler & Snow

[57] ABSTRACT

A portable apparatus for irrigation of the intestines and colon wherein an undulating stream of warm water is injected by an enema tip vertically reciprocating in and out of the lower end of the rectum in timed relation allowing for simultaneous intermittent discharge of waste products therefrom.

2 Claims, 8 Drawing Figures

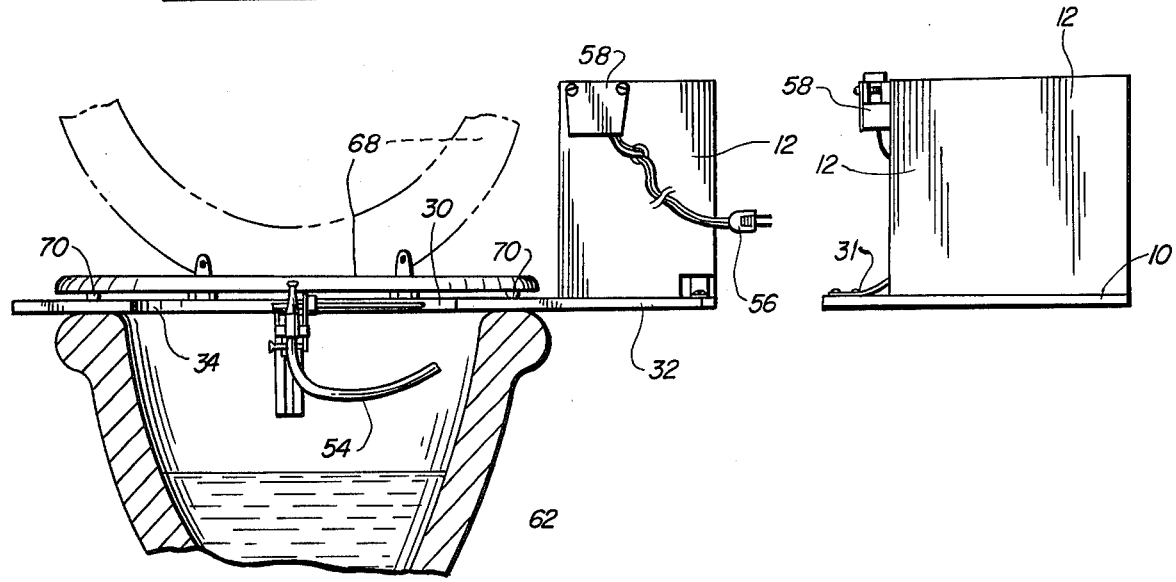
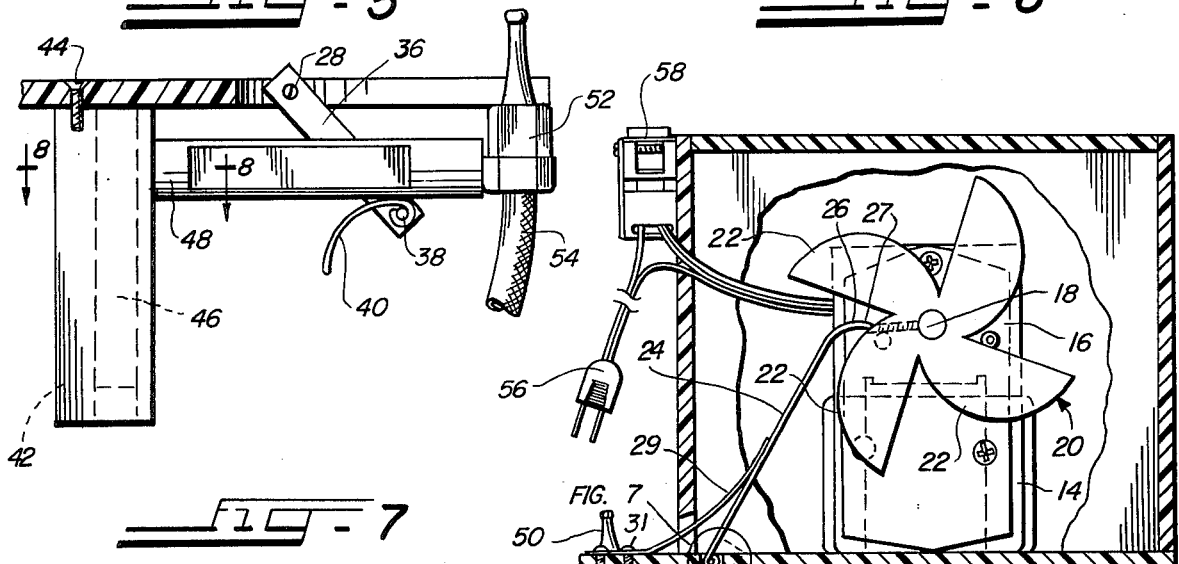

UNDULATING RECTAL FLUSHING APPARATUS

Prior Art

U.S. Pat. Nos.: 1,983,293, December 1934, Hudgings; 2,478,876, August 1949, Nelson; 2,506,183, May 1950, Touchberry; 3,042,039, July 1962, Dahlstrom; 3,678,932, July 1972, Hudson; 2,328,893, September 1943, Conrad.

This invention is an improvement on my U.S. Pat. No. 3,762,410 granted Oct. 2, 1973. The foregoing prior art was cited during the prosecution of the above patent. (See Class 128, subclass 227.)

SUMMARY OF THE INVENTION

This invention is a portable irrigation apparatus for the colon and intestines with the patient sitting in a comfortable position on a toilet seat, the unit lying therebelow on the rim of the toilet bowl, whereby an undulating stream of warm water is injected by an enema tip which reciprocates in and out of the lower end of the rectum. This device is wholly portable and thus can be readily used from one point to another with considerable ease. This cannot be accomplished with the known prior art devices.

BRIEF DESCRIPTION OF THE DRAWINGS

FIG. 3 is a cross-sectional view taken on the lines 3—3 of FIG. 2;

FIG. 4 is an end elevational view taken on the lines 4—4 of FIG. 2;

FIG. 5 is a cross-sectional view taken on the lines 5—5 of FIG. 2;

FIG. 6 is a cross-sectional view taken on the lines 6—6 of FIG. 2;

FIG. 7 is a cross-sectional view taken in the circle labeled "FIG. 7" in FIG. 6; and FIG. 8 is a cross-sectional view taken on the lines 8—8 of FIG. 5.

DETAILED DESCRIPTION OF THE DRAWINGS

Figure 1:
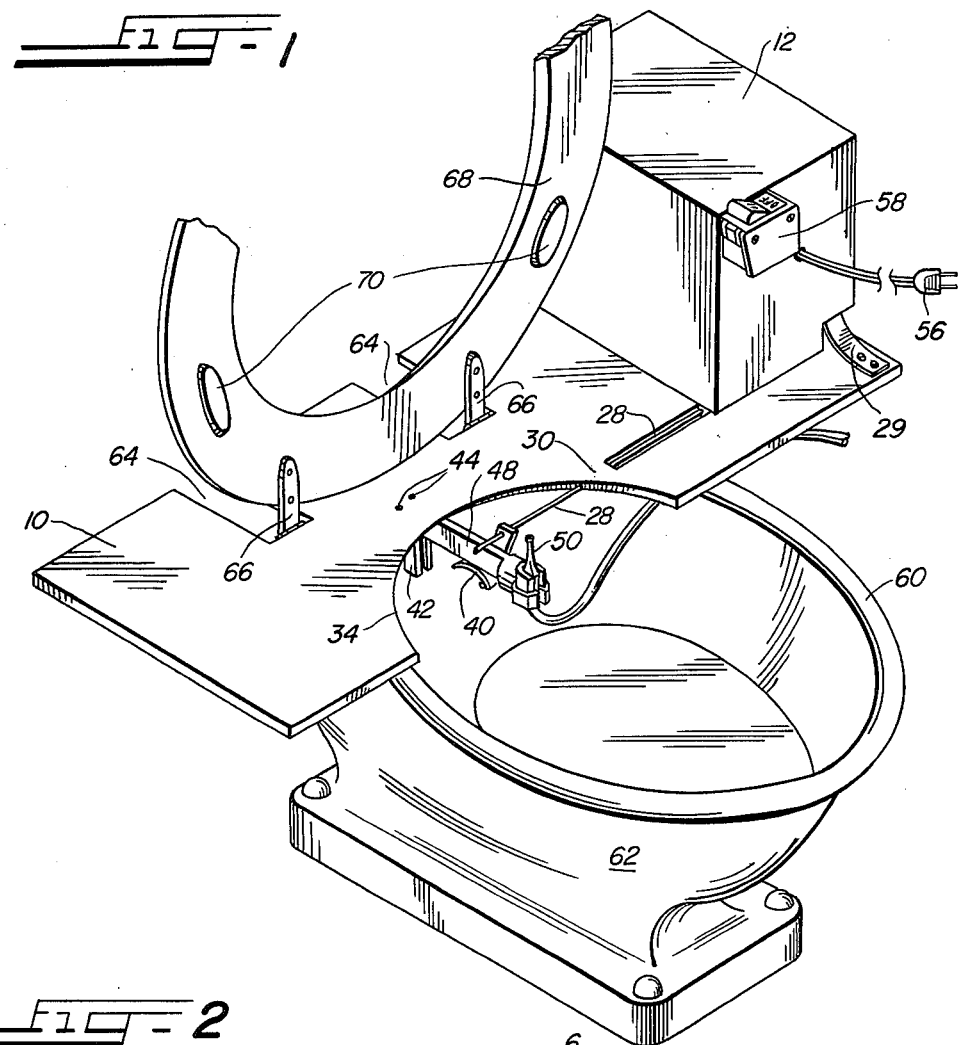
FIG. 1 is a perspective view of the invention shown positioned on the rim of a toilet bowl, the toilet seat shown broken away.

The device of the present invention comprises an enlarged rectangular plate 10 having a housing 12 anchored to one end thereof and extending upwardly from the plate 10 which houses a motor 14 having its shaft connected to reduction gears in gear housing 16. A shaft 18 from the reducing gears carries the circular cam 20 having four lobes 22. The cam is mounted to rotate on the shaft 18.

Figure 2:
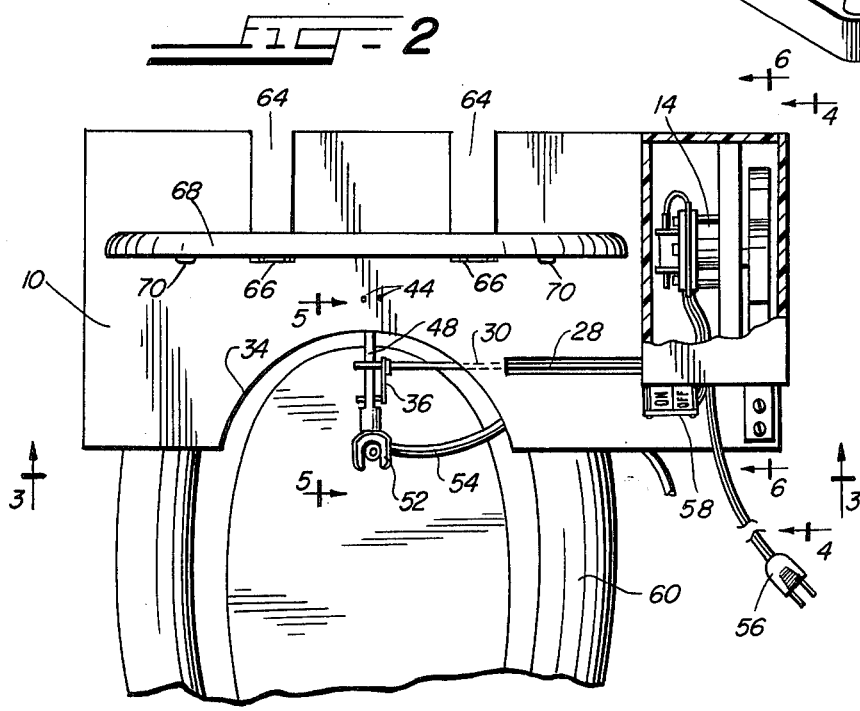
FIG. 2 is a top elevational view thereof with parts broken away.

A cam follower 24 having one end bent on a radius 26 has its free end 27 bearing on one of the lobes 22, as shown in FIG. 6. To insure positive contact of the follower tip 27, a spring 29 lies against the follower body, as shown in FIG. 6, with the opposite end anchored at 31 to plate 10. The other or free end of the follower 24 is fixedly secured to an elongated rod shaft 28. The shaft 28 extends laterally, as shown in FIGS. 1–3, and is mounted in elongated spaced bearings 30, 32 formed by drilling the plate 10 lengthwise, one adjacent the follower 24 and the other adjacent the semi-circular cutout 34 in plate 10 to keep the shaft 28 in a horizontal position. The free end of shaft 28 is provided with a depending adjustable crank arm 36 anchored thereto and shiftable by reciprocation of the shaft 28. The free end of the crank arm 36 has right angled rod 38 secured thereto at one end to which a wide curved plate 40 is secured and extends at right angles thereto. A vertically extending guideway 42 depends from the under side of plate 10 and is anchored thereto by screws 44 to slidingly support a slider bar 46 for reciprocating movement in a vertical direction.

A cross arm 48 is anchored to the upper end of slide bar 46 and extends at right angles thereto and a bracket 52 is secured to the free end thereof. An enema tip 50 is carried in a support bracket 52 and is removably secured thereto. A flexible hose 54 is connected at one end to a warm water supply (not shown) and the opposite end is connected to the enema tip 50.

The motor 14 is connected to a source of current through plug 56 with an on-off switch 58 in the circuit. When the motor is energized, the cam 20 will rotate and with the rise and fall of the follower 24, cause the rod shaft 28 to reciprocate as one end of the follower is secured to one end of the rod shaft.

The reciprocating shaft 28 will also reciprocate the crank arm 36 which, in turn, because of the curved arm 40, will cause the rod 48 to reciprocate vertically.

The plate 10 is seated on the rim 60 of the toilet bowl 62 with the parallel rectangular cutouts 64 spanning the hinges 66 of toilet seat 68. When the toilet seat 68 is lowered to the rim 60, the rear bumpers 70 will seat on the upper surface of plate 10 to support the plate in horizontal position. Thus the cutout 34 will extend forward of the rear end of rim 60 to protect the guideway 42 slider bar 46.

Thus, when a patient is sitting on the toilet seat in a comfortable position, he merely energizes the motor by pressing the on button of the switch 58. With warm water flowing in tube 54, the enema tip will reciprocate in and out of the rectum in an undulating motion with the warm soft jet of water projecting in the alimentary canal and allowing for simultaneous intermittent discharge of waste products therefrom.

It will be understood that the device is so constructed that the enema tip will automatically position itself to be readily insertable in the anus as the enema tip extends above the plate 10 at the top of the stroke of the slide bar.

Upon completion of the treatment, the patient merely deenergizes the motor by moving the switch to off position and is free to arise from the seat 68. The device may now be readily removed from the rim of the toilet bowl, sanitized, and is ready for use by another patient.

The slide bar 46, the guideway 42 and the rod 46 are constructed of plastic, preferably Teflon or the like, for ease in movement to eliminate lubrication. Also, the plate 10 and housing 12 are preferably made from clear plastic for ease of cleaning.

Although but one specific embodiment of this invention is herein shown and described, it will be understood that details of the construction shown may be altered or omitted without departing from the spirit of the invention as defined by the following claims.

I claim:

1. A portable apparatus for irrigation of the colon and intestines removably positioned on the rim of a toliet bowl and held in position by the usual toilet seat comprising:
   (a) a base plate,
      (1) having a semicircular cutout portion, and (2) a pair of spaced slots therein positioned opposite the cutout;
(b) an enclosed housing anchored on the upper side and on one end of said plate;
(c) a motor in said housing operatively connected to:
 (1) a reduction gearing,
 (2) a shaft extending from said reduction gearing;
(d) a circular cam fixedly mounted to said shaft,
 (1) said cam having a plurality of lobes, each lobe having a curved rising work face and a falling work face;
(e) an elongated rod shaft extending through said plate to medially of said cutout portion;
(f) an elongated cam follower having one end positionable on said cam, and its other end fixedly mounted to one end of said rod shaft;
(g) an adjustable crank arm secured to the other end of said rod shaft, having a right angled arm at its free end and supporting one end of a curved wide arm extending at right angles thereto;
(h) a vertically extending guideway secured to and depending from said plate;
(i) a slide bar supported in said guideway,
 (1) a cross arm secured at one end to said slide bar and extending at right angles to said guideway and having a portion thereof lying on said curved arm,
 (2) a support bracket anchored to the free end of said rod;
(j) an enema tip removably mounted in said bracket and directed to jet warm fluid vertically for vertically reciprocative motion relative to said base plate.

2. The device according to claim 1 wherein a spring retains said one end of the follower on said lobes when said cam rotates.

* * * * *